US010822400B2

(12) United States Patent
Laporte et al.

(10) Patent No.: US 10,822,400 B2
(45) Date of Patent: Nov. 3, 2020

(54) DYNAMIN 2 INHIBITOR FOR THE TREATMENT OF DUCHENNE'S MUSCULAR DYSTROPHY

(71) Applicants: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

(72) Inventors: Jocelyn Laporte, Strasbourg (FR); Belinda Cowling, Kaltenhouse (FR)

(73) Assignees: UNIVERSITE DE STRASBOURG, Strasbourg (FR); CENTRE NATIONAL DE LA RECHERCHE SCIENTIFIQUE, Paris (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 0 days.

(21) Appl. No.: 15/568,007

(22) PCT Filed: Apr. 22, 2016

(86) PCT No.: PCT/EP2016/059090
§ 371 (c)(1),
(2) Date: Oct. 20, 2017

(87) PCT Pub. No.: WO2016/170162
PCT Pub. Date: Oct. 27, 2016

(65) Prior Publication Data
US 2018/0142008 A1    May 24, 2018

(30) Foreign Application Priority Data

Apr. 22, 2015 (EP) ..................... 15305615

(51) Int. Cl.
*C07K 16/18* (2006.01)
*C12N 15/113* (2010.01)
*A61P 21/00* (2006.01)
*A61K 45/06* (2006.01)

(52) U.S. Cl.
CPC .............. *C07K 16/18* (2013.01); *A61K 45/06* (2013.01); *A61P 21/00* (2018.01); *C12N 15/1137* (2013.01); *C12Y 306/05005* (2013.01); *A61K 2300/00* (2013.01); *C12N 2310/11* (2013.01); *C12N 2310/12* (2013.01); *C12N 2310/14* (2013.01)

(58) Field of Classification Search
None
See application file for complete search history.

(56) References Cited

FOREIGN PATENT DOCUMENTS

JP        2014-520813       8/2014
WO     WO 2012/164234    12/2012

OTHER PUBLICATIONS

McFarland et al. RNA Interference-Mediated Knockdown of Dynamin 2 Reduces Endocannabinoid Uptake into Neuronal dCAD Cells. Molecular Pharmacology, 2008; 74:101-108. (Year: 2008).*
Vajdos et al. Comprehensive Functional Maps of the Antigen-binding Site of an Anti-ErbB2 Antibody Obtained with Shotgun Scanning Mutagenesis. Journal of Molecular Biology Jul. 5, 2002;320(2):415-28 at 416 (Year: 2002).*
Brown et al. Toerance to single, but not multiple, amino acid replacements in antibody Vh CDR2. Journal of Immunology, May 1996 ; 156(9):3285-91 (Year: 1996).*
Aagaard et al. RNAi therapeutics: principles, prospects and challenges. Advanced Drug Delivery Reviews 59 (2007) 75-86 (Year: 2007).*
Warzocha et al. Antisense Strategy: Biological Utility and Prospects in the Treatment of Hematological Malignancies. Leukemia and Lymphoma, 1997; 24(3-4):267-281 (Year: 1997).*
Ma. Animal models of disease. Modern Drug Discovery 2004, 7(6): 30-36 (Year: 2004).*
Aagaard et al. Advanced Drug Delivery Reviews 59 (2007) 75-86 (Year: 2007).*
Warzocha et al. Leukemia and Lymphoma, vol. 24. pp. 267-281 (Year: 1997).*
Chakraborty et al. Mol Ther Nucleic Acids. Sep. 15, 2017;8:132-143 (Year: 2017).*
Alexander, M. S. et al. "MicroRNA-199a is induced in dystrophic muscle and affects WNT signaling, cell proliferation, and myogenic differentiation" *Cell Death and Differentiation*, Sep. 2013, pp. 1194-1208, vol. 20, No. 9.
Al-Zaidy, S. et al. "Gene Therapy for Muscular Dystrophy: Moving the Field Forward" *Pediatric Neurology*, Nov. 2014, pp. 607-618, vol. 51, No. 5.
Cowling, B. S. et al. "Reducing dynamin 2 expression rescues X-linked centronuclear myopathy" *The Journal of Clinical Investigation*, Mar. 3, 2014, pp. 1350-1363, vol. 124, No. 3.
Singleton, P. A. et al. "Dynamin 2 and c-Abl Are Novel Regulators of Hyperoxia-mediated NADPH oxidase Activation and Reactive Oxygen Species Production in Caveolin-enriched Microdomains of the Endothelium" *The Journal of Biological Chemistry*, pp. 34964-34975, vol. 284, No. 50.
Written Opinion in International Application No. PCT/EP2016/059090, dated Jul. 5, 2016, pp. 1-5.

(Continued)

*Primary Examiner* — Vanessa L. Ford
*Assistant Examiner* — Sandra E Dillahunt
(74) *Attorney, Agent, or Firm* — Saliwanchik, Lloyd & Eisenschenk (57) ABSTRACT

The present disclosure relates to an inhibitor of Dynamin 2 or composition comprising the same for use in the treatment of Duchenne's muscular dystrophy.

10 Claims, 2 Drawing Sheets

Specification includes a Sequence Listing.

(56) References Cited

OTHER PUBLICATIONS

Gong, C. et al. "Dynamin2 downregulation delays EGFR endocytic trafficking and promotes EGFR signaling and invasion in hepatocellular carcinoma" *Am J Cancer Res*, 2015, pp. 702-713, supplementary figure 1 (1 page), vol. 5, No. 2.

Cowling, B. S. et al. "365. Reducing Dynamin 2 Rescues a Severe Congenital Myopathy in Mice" *Molecular Therapy*, May 2014, p. S139, vol. 22, No. 1.

* cited by examiner

SEQUENCE LISTING

```
<160> NUMBER OF SEQ ID NOS: 28

<210> SEQ ID NO 1
<211> LENGTH: 3714
<212> TYPE: DNA
<213> ORGANISM: Homo sapiens

<400> SEQUENCE: 1
gaggtcgctc gggtcgggtg tcgcctgaga accggatgag gcggcgaccg tgaggccgag      60
ccgggagcgg gcgtcttgcc gaggcccggg cgggcgggga gcaacggcta cagacgccgc     120
ggggccaggt cgttgagggt cggcggcggg cgaggagcgc agggcgctcg ggccggggc      180 cgccggcgcc atgggcaacc gcgggatgga agagctgatc ccgctggtca acaaactgca     240
ggacgccttc agctccatcg gccagagctg ccacctggac ctgccgcaga tcgctgtagt     300
gggcggccag agcgccggca agagctcggt gctggagaac ttcgtgggcc gggacttcct     360
tccccgcggt tcaggaatcg tcacccggcg gcctctcatt ctgcagctca tcttctcaaa     420
aacagaacat gccgagtttt tgcactgcaa gtccaaaaag tttacagact ttgatgaagt     480
ccggcaggag attgaagcag agaccgacag ggtcacgggg accaacaaag gcatctcccc     540
agtgcccatc aaccttcgag tctactcgcc acacgtgttg aacttgaccc tcatcgacct     600
cccgggtatc accaaggtgc ctgtgggcga ccagcctcca gacatcgagt accagatcaa     660
ggacatgatc ctgcagttca tcagccggga gagcagcctc attctggctg tcacgccgc      720 caacatggac ctggccaact ccgacgccct caagctggcc aaggaagtcg atcccaagg      780 cctacggacc atcggtgtca tcaccaagct tgacctgatg gacgagggca ccgacgccag     840
ggacgtcttg gagaacaagt tgctcccgtt gagaagaggc tacattggcg tggtgaaccg     900
cagccagaag gatattgagg gcaagaagga catccgtgca gcactggcag ctgagaggaa     960
gttcttcctc tcccacccgg cctaccggca catggccgac cgcatgggca cgccacatct    1020
gcagaagacg ctgaatcagc aactgaccaa ccacatccgg gagtcgctgc cggccctacg    1080
tagcaaacta cagagccagc tgctgtccct ggagaaggag gtggaggagt acaagaactt    1140
tcggcccgac gaccccaccc gcaaaaccaa agccctgctg cagatggtcc agcagtttgg    1200
ggtggatttt gagaagagga tcgagggctc aggagatcag gtggacactc tggagctctc    1260 cggggcgcc cgaatcaatc gcatcttcca cgagcggttc ccatttgagc tggtgaagat    1320
```

```
ggagtttgac gagaaggact tacgacggga gatcagctat gccattaaga acatccatgg    1380
agtcaggacc gggcttttca ccccggactt ggcattcgag gccattgtga aaaagcaggt    1440
cgtcaagctg aaagagccct gtctgaaatg tgtcgacctg gttatccagg agctaatcaa    1500
tacagttagg cagtgtacca gtaagctcag ttcctacccc cggttgcgag aggagacaga    1560
gcgaatcgtc accacttaca tccgggaacg ggaggggaga acgaaggacc agattcttct    1620
gctgatcgac attgagcagt cctacatcaa cacgaaccat gaggacttca tcgggttttgc    1680 caactgttac tatactgagc agctggtgac ctgtgcccag cagaggagca cgcagctgaa    1740
caagaagaga gccatcccca tcaggggga gatcctggtg atccgcaggg gctggctgac    1800
catcaacaac atcagcctga tgaaaggcgg ctccaaggag tactggtttg tgctgactgc    1860
cgagtcactg tcctggtaca aggatgagga ggagaaagag aagaagtaca tgctgcctct    1920
ggacaacctc aagatccgtg atgtggagaa gggcttcatg tccaacaagc acgtcttcgc    1980
catcttcaac acggagcaga gaaacgtcta caaggacctg cggcagatcg agctggcctg    2040
tgactcccag gaagacgtgg acagctgaaa ggcctcgttc ctccgagctg cgtctaccc    2100 cgagaaggac caggcagaaa cgaggatgg ggcccaggag aacaccttct ccatggaccc    2160
ccaactggag cggcaggtgg agaccattcg caacctggtg gactcatacg tggccatcat    2220
caacaagtcc atccgcgacc tcatgccaaa gaccatcatg cacctcatga tcaacaatac    2280
gaaggccttc atccaccacg agctgctggc ctacctatac tcctcggcag accagagcag    2340
cctcatggag gagtcggctg accaggcaca gcggcgggac gacatgctgc catgtacca    2400 tgccctcaag gaggcgctca acatcatcgg tgacatcagc accagcactg tgtccacgcc    2460 tgtaccccg cctgtcgatg acacctggct ccagagcgcc agcagccaca gccccactcc    2520
acagcgccga ccggtgtcca gcatacaccc ccctggccgg cccccagcag tgaggggccc    2580
cactccaggg cccccctga ttcctgttcc cgtggggca gcagcctcct tctcggcgcc    2640
cccaatccca tccggcctg gaccccagag cgtgtttgcc aacagtgacc tcttcccagc    2700
cccgcctcag atcccatctc ggccagttcg gatccccca gggattcccc caggagtgcc    2760
cagcagaaga cccccctgctg cgcccagccg gccaccatt atccgcccag ccgagccatc    2820
cctgctcgac taggcctcga gggggcgtg ctctcgggg ggcctcacgc acccgcggcg    2880
caggagcttc agtggtctgg ggcctccgc cgccctatg ctgggaccag gctcccagtg    2940
ggcagccctg gcctcttcct taacgctggc cccggtccag ggccggcccc tgtgcctggc    3000
tggacaccgc actgcgcaaa gggggccctgg agctccaggc agggggcgct ggggtgttgc    3060
actttggggg atggagtctc agggtggcag aggggggacc agaaaccctttg acaccatcct    3120 gaatgagggg tccagcctgg gggggactct accaaggtct tcttgggctg gaaagccca    3180 tgtagggcag gccttctata agtgcgggca ccaagggcgc ctacatcccc aggccttgct    3240
ggggtgcagg gtatatcaa cttcccatta gcaggagctc cccagcggca agcctggccc    3300
agtgggctcg gtagtgccca gctggcaggc ctgaggtgta catagtcctt cccggccata    3360
ttaaccacac agcctgagcc tggcccagcc tcggctgcca gaggtgcctt tgctaggccc    3420
ggagccgttg gccgggccg gccttgccct attcctctcc tcctcctcct cctgggtccc    3480
ccagggtggc tgggcttggg ctatgtgggt ggtggtggcg ggggtcttg ggggcctctc    3540 agctcccgcc catgcctccc tgatgggtgg gccagggcg gcctctctct gaggagacct    3600
cacccactcc tcgctcagtt tgaccactgt aagtgcctgc actctgtatt ctattaataa    3660
actaaaataa agggaagacg ctgctggtgg ctgctgaaaa aaaaaaaaaa aaaa          3714
```

-continued

<210> SEQ ID NO 2
<211> LENGTH: 23
<212> TYPE: DNA
<213> ORGANISM: artificial sequence
<220> FEATURE:
<223> OTHER INFORMATION: iRNA

<400> SEQUENCE: 2
aaggacatga tcctgcagtt cat                                                23

<210> SEQ ID NO 3
<211> LENGTH: 23
<212> TYPE: DNA
<213> ORGANISM: artificial sequence
<220> FEATURE:
<223> OTHER INFORMATION: iRNA

<400> SEQUENCE: 3
aagaggctac attggcgtgg tga                                                23

<210> SEQ ID NO 4
<211> LENGTH: 23
<212> TYPE: DNA
<213> ORGANISM: artificial sequence
<220> FEATURE:
<223> OTHER INFORMATION: iRNA

<400> SEQUENCE: 4
aggtggacac tctggagctc tcc                                                23

<210> SEQ ID NO 5
<211> LENGTH: 23
<212> TYPE: DNA
<213> ORGANISM: artificial sequence
<220> FEATURE:
<223> OTHER INFORMATION: iRNA

<400> SEQUENCE: 5
aagaagtaca tgctgcctct gga                                                23

<210> SEQ ID NO 6
<211> LENGTH: 23
<212> TYPE: DNA
<213> ORGANISM: artificial sequence
<220> FEATURE:
<223> OTHER INFORMATION: iRNA

<400> SEQUENCE: 6
aacgtctaca aggacctgcg gca                                                23

<210> SEQ ID NO 7
<211> LENGTH: 23
<212> TYPE: DNA
<213> ORGANISM: artificial sequence
<220> FEATURE:
<223> OTHER INFORMATION: iRNA

<400> SEQUENCE: 7 aggagaaacac cttctccatg gac                                               23

<210> SEQ ID NO 8
<211> LENGTH: 21
<212> TYPE: DNA
<213> ORGANISM: artificial sequence
<220> FEATURE:

```
<223> OTHER INFORMATION: iRNA

<400> SEQUENCE: 8
aactgttact atactgagca g                                              21

<210> SEQ ID NO 9
<211> LENGTH: 19
<212> TYPE: DNA
<213> ORGANISM: artificial sequence
<220> FEATURE:
<223> OTHER INFORMATION: iRNA

<400> SEQUENCE: 9
tgccaactgt tactatact                                                 19

<210> SEQ ID NO 10
<211> LENGTH: 19
<212> TYPE: DNA
<213> ORGANISM: artificial sequence
<220> FEATURE:
<223> OTHER INFORMATION: iRNA

<400> SEQUENCE: 10
gaagagctga tcccgctgg                                                 19

<210> SEQ ID NO 11
<211> LENGTH: 19
<212> TYPE: DNA
<213> ORGANISM: artificial sequence
<220> FEATURE:
<223> OTHER INFORMATION: iRNA

<400> SEQUENCE: 11
gcacgcagct gaacaagaa                                                 19

<210> SEQ ID NO 12
<211> LENGTH: 19
<212> TYPE: DNA
<213> ORGANISM: artificial sequence
<220> FEATURE:
<223> OTHER INFORMATION: iRNA

<400> SEQUENCE: 12
ggacttacga cgggagatc                                                 19

<210> SEQ ID NO 13
<211> LENGTH: 19
<212> TYPE: DNA
<213> ORGANISM: artificial sequence
<220> FEATURE:
<223> OTHER INFORMATION: iRNA

<400> SEQUENCE: 13
ggatattgag ggcaagaag                                                 19

<210> SEQ ID NO 14
<211> LENGTH: 19
<212> TYPE: DNA
<213> ORGANISM: artificial sequence
<220> FEATURE:
<223> OTHER INFORMATION: iRNA

<400> SEQUENCE: 14
ggaccaggca gaaaacgag                                                 19
```

```
<210> SEQ ID NO 15
<211> LENGTH: 19
<212> TYPE: DNA
<213> ORGANISM: artificial sequence
<220> FEATURE:
<223> OTHER INFORMATION: iRNA

<400> SEQUENCE: 15
gcgaatcgtc accacttac                                               19

<210> SEQ ID NO 16
<211> LENGTH: 20
<212> TYPE: DNA
<213> ORGANISM: artificial sequence
<220> FEATURE:
<223> OTHER INFORMATION: shRNA

<400> SEQUENCE: 16
aaccgcggga tggaagagct                                              20

<210> SEQ ID NO 17
<211> LENGTH: 21
<212> TYPE: DNA
<213> ORGANISM: artificial sequence
<220> FEATURE:
<223> OTHER INFORMATION: shRNA

<400> SEQUENCE: 17
aacttgaccc tcatcgacct c                                            21

<210> SEQ ID NO 18
<211> LENGTH: 19
<212> TYPE: DNA
<213> ORGANISM: artificial sequence
<220> FEATURE:
<223> OTHER INFORMATION: shRNA

<400> SEQUENCE: 18
tcggtgtcat caccaagct                                               19

<210> SEQ ID NO 19
<211> LENGTH: 19
<212> TYPE: DNA
<213> ORGANISM: artificial sequence
<220> FEATURE:
<223> OTHER INFORMATION: shRNA

<400> SEQUENCE: 19
tgccaactgt ttctatact                                               19

<210> SEQ ID NO 20
<211> LENGTH: 21
<212> TYPE: DNA
<213> ORGANISM: artificial sequence
<220> FEATURE:
<223> OTHER INFORMATION: shRNA

<400> SEQUENCE: 20
aactgtttct atactgagga g                                            21

<210> SEQ ID NO 21
<211> LENGTH: 21
<212> TYPE: DNA
<213> ORGANISM: artificial sequence
<220> FEATURE:
<223> OTHER INFORMATION: shRNA
```

<400> SEQUENCE: 21
tttctatact gaggagctgg t                                              21

<210> SEQ ID NO 22
<211> LENGTH: 19
<212> TYPE: DNA
<213> ORGANISM: artificial sequence
<220> FEATURE:
<223> OTHER INFORMATION: shRNA

<400> SEQUENCE: 22
gcacgcagct gaacaagaa                                                 19

<210> SEQ ID NO 23
<211> LENGTH: 23
<212> TYPE: DNA
<213> ORGANISM: artificial sequence
<220> FEATURE:
<223> OTHER INFORMATION: shRNA

<400> SEQUENCE: 23
aagaagtaca tgctgcctct gga                                            23

<210> SEQ ID NO 24
<211> LENGTH: 20
<212> TYPE: DNA
<213> ORGANISM: artificial sequence
<220> FEATURE:
<223> OTHER INFORMATION: shRNA

<400> SEQUENCE: 24
aacaccttct ccatggaccc                                                20

<210> SEQ ID NO 25
<211> LENGTH: 21
<212> TYPE: DNA
<213> ORGANISM: artificial sequence
<220> FEATURE:
<223> OTHER INFORMATION: shRNA

<400> SEQUENCE: 25
ccattatccg cccagccgag c                                              21

<210> SEQ ID NO 26
<211> LENGTH: 30
<212> TYPE: DNA
<213> ORGANISM: artificial sequence
<220> FEATURE:
<223> OTHER INFORMATION: antisense RNA

<400> SEQUENCE: 26
gtcacccgga ggcctctcat tctgcagctc                                     30

<210> SEQ ID NO 27
<211> LENGTH: 33
<212> TYPE: DNA
<213> ORGANISM: artificial sequence
<220> FEATURE:
<223> OTHER INFORMATION: antisense RNA

<400> SEQUENCE: 27
acacactaga gttgtctggt ggagcccgca tca                                 33

<210> SEQ ID NO 28
<211> LENGTH: 10

```
<212> TYPE: PRT
<213> ORGANISM: artificial Sequence
<220> FEATURE:
<223> OTHER INFORMATION: inhibitory peptide

<400> SEQUENCE: 28

Gln Val Pro Ser Arg Pro Asn Arg Ala Pro
1               5                   10
```

DYNAMIN 2 INHIBITOR FOR THE TREATMENT OF DUCHENNE'S MUSCULAR DYSTROPHY

CROSS-REFERENCE TO RELATED APPLICATION

This application is the U.S. national stage application of International Patent Application No. PCT/EP2016/059090, filed Apr. 22, 2016.

The Sequence Listing for this application is labeled "Seq-List.txt" which was created on Oct. 17, 2017 and is 10 KB. The entire content of the sequence listing is incorporated herein by reference in its entirety.

FIELD OF THE INVENTION

The present disclosure relates to an inhibitor of Dynamin 2 or composition comprising the same for use in the treatment of Duchenne's muscular dystrophy.

BACKGROUND OF THE INVENTION

Duchenne's Muscular Dystrophy (DMD) is the most common myopathy in children. DMD patients develop a dystrophic phenotype in muscle. DMD is a severe X-linked disorder, with progressive muscle wasting and weakness affecting almost all muscles, and normally results in premature death due to cardiorespiratory failure. Despite extensive research into therapies for DMD many of which targeting the expression of dystrophin (reviewed in Al-Zaidy, S., L. Rodino-Klapac and J. R. Mendell (2014). "Gene therapy for muscular dystrophy: moving the field forward." *Pediatr Neurol* 51(5): 607-618), no effective treatment has yet been developed for this devastating disease.

DMD is due to mutations in dystrophin, resulting in loss of dystrophin protein expression. Dystrophin forms the mechanical link between the contractile apparatus and the plasma membrane of the muscle fiber. In DMD patients the loss of dystrophin expression causes a disruption of the normal force transmission, which places a large amount of stress on the fiber and results in muscle fiber damage. Effective therapies are required for DMD patients which target the physiological muscle force, and therefore improved muscle function. Most therapeutic approaches for DMD have targeted the mutated gene, dystrophin, as to attempt to improve the expression of all/part of dystrophin.

Recently, it has been disclosed a novel potential therapy for X-linked centronuclear myopathy (XLCNM) patients by reduction of DNM2 expression. This novel approach was based on the findings that reducing dynamin 2 (DNM2) expression can rescue the XLCNM, also called myotubular myopathy, phenotype in Mtm1$^{-/y}$ mice.

The inventors have discovered a significant improvement in specific muscle force at several ages by reducing DNM2 in mdx mice, which are the classic mouse model used for preclinical DMD research. Furthermore, an improvement in resistance to contraction-induced muscle injury, confirms the physiological significance of this finding. Therefore, it is herein provided a novel therapeutic approach for the treatment of Duchenne's muscular dystrophy by reducing DNM2 expression.

SUMMARY OF THE INVENTION

In a first aspect, the present invention concerns an inhibitor of Dynamin 2 for use in the treatment of DMD.

The present invention also concerns a pharmaceutical composition comprising an inhibitor of Dynamin 2 and a pharmaceutically acceptable carrier/excipient for use in the treatment of DMD.

The present invention further concerns a method for the treatment of DMD, wherein the method comprises the step of administering into a subject in need of such treatment a therapeutically efficient amount of a Dynamin 2 inhibitor.

Finally, the present invention concerns the use of a Dynamin 2 inhibitor for the preparation of a pharmaceutical composition for the treatment of DMD.

The Dynamin 2 inhibitor is preferably selected from the group consisting of an antibody directed against Dynamin 2, a nucleic acid molecule interfering specifically with Dynamin 2 expression, a nucleic acid or a nuclease engineered to target the DNM2 gene and to deliver nucleases using genome editing therapy, and a small molecule inhibiting the Dynamin 2 activity, expression or function. In a preferred embodiment, the Dynamin 2 inhibitor is selected from the group consisting of a nucleic acid molecule interfering specifically with Dynamin 2 expression. In a particular embodiment, the Dynamin 2 inhibitor is an RNAi, an antisense nucleic acid or a ribozyme interfering specifically with Dynamin 2 expression.

In a more specific embodiment, the Dynamin 2 inhibitor is a siRNA, shRNA or an antisense snRNA. In another particular embodiment, the dynamin 2 inhibitor is a DNA, mRNA or a nuclease engineered to target the DNM2 gene and to deliver nucleases using genome editing therapy.

A further object of the invention relates to a method of screening for identifying compounds useful for the treatment of DMD comprising:
a) Providing or obtaining a candidate compound,
b) Determining whether said candidate compound inhibits the activity/expression of Dynamin 2, and
c) Selecting said candidate compound if it inhibits the activity/expression of Dynamin 2.

The method for screening or identifying a molecule suitable for the treatment of DMD can optionally further comprise the step of administering in vivo or in vitro the selected molecule in a DMD non-human animal model or a part thereof (tissue or cells) and analyzing the effect on the myopathy onset or progression.

These and other objects and embodiments of the invention will become more apparent after the detailed description of the invention.

BRIEF DESCRIPTION OF THE DRAWINGS

FIG. 3. (A) Specific muscle force (sPo) was initially measured in the tibialis anterior muscle from mdx-/y (white) and mdx-/yDnm2+/- (black) mice. (B) The tibialis anterior muscle was then subjected to 9 lengthening contractions. Results for mdx−/y (solid black line) and mdx−/yDnm2+/− (dashed black line) mice are displayed as a percentage of initial force (%), after 0, 3, 6 and 9 lengthening contractions. (C) An intramuscular injection of AAV-shRNA targeting DNM2 (black) or a scrambled control sequence (white) was performed into the tibialis anterior of mdx−/y mice at 3 weeks of age. Specific muscle force (sPo) was measured in the tibialis anterior muscle at 3 months of age. (D) The tibialis anterior muscle was then subjected to 9 lengthening contractions as in (B), AAV shRNA control (solid black line) and AAV shRNA DNM2 (dashed black line).

DETAILED DESCRIPTION

Unless otherwise defined, all technical and scientific terms used herein have the same meaning as commonly understood by one of ordinary skill in the art to which this invention belongs. The Dynamin 2 is encoded by the DNM2 gene (Gene ID 1785). More precisely, the DNM2 gene is located from base pair 10,919,884 to base pair 10,942,586 on chromosome 19 (GRCh37/hg19 release) or from 10,718,053 to 10,831,910 base pairs on the NC_000019.10 location (GRCh38/hg19). The dynamin 2 gene or gene products are also known by other names, including but not limited to CMTDI1, CMTDIB, DI-CMTB, DYN2, DYN2_HUMAN, dynamin II, DYNII.

Dynamin 2 Inhibitors

As used herein, the term "Dynamin 2 inhibitor" refers to any molecule able to decrease specifically the expression of Dynamin 2 or inhibit the Dynamin 2 activity or function. Preferably, such a Dynamin 2 inhibitor is a direct inhibitor, meaning that it interacts directly with either the Dynamin 2 protein or a nucleic acid encoding said Dynamin 2 or a part thereof. The Dynamin 2 inhibitors according to the invention are capable of inhibiting or decreasing the functional activity of Dynamin 2 in vivo and/or in vitro. The inhibitor may inhibit the functional activity of Dynamin 2 by at least about 30%, preferably by at least about 50%, preferably by at least about 70, 75 or 80%, still preferably by 85, 90, or 95%. In particular, the inhibitor may inhibit Dynamin 2 expression by at least about 10%, preferably by at least about 30%, 35%, 40%, 45%, preferably by at least about 50%, preferably by at least about 70, 75 or 80%.

A Dynamin 2 inhibitor of the invention may act by blocking and/or inhibiting the activity or function of Dynamin 2. This may for example be achieved by inhibiting the enzymatic activity of Dynamin 2. Functional or enzymatic activity of Dynamin 2 may be readily assessed by one skilled in the art according to known methods by testing for example the GTPase activity or the function of Dynamin 2 in clathrin-mediated endocytosis (Macia E. et al., Dynasore, a cell-permeable inhibitor of dynamin: Developmental cell 10, 839-850, June 2006). For inhibitors of GTPase activity or lipid binding, subcellular localization, clathrin mediated endocytosis, synaptic vesicle endocytosis, one can use the method described in McCluskey et al, Traffic, 2013; McGeachie et al, ACS Chem Biol, 2013. For Dynamin 2 GTPase activity, oligomerisation, lipid binding, one can use the methods described in Wang et al J Biol Chem 2010; or Kenniston and Lemmon, Embo J, 2010.

Figure 1:
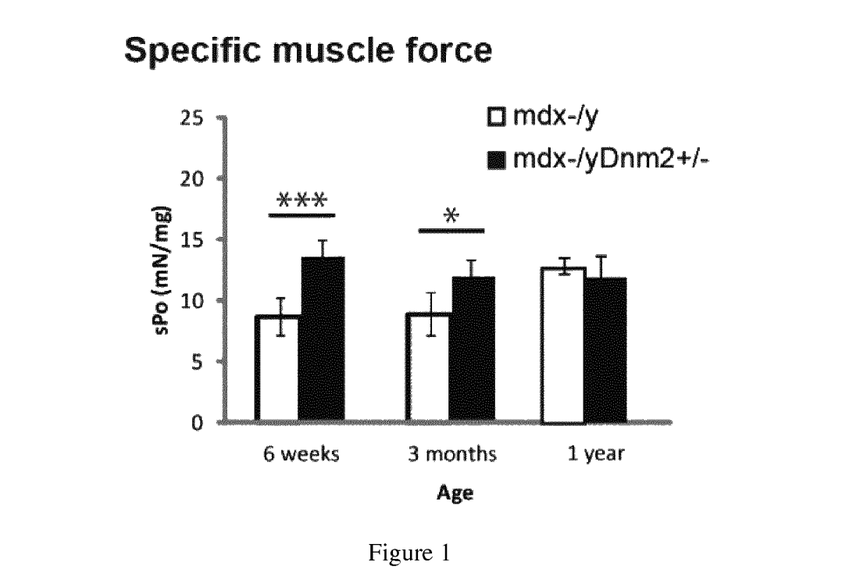
FIG. 1. Specific muscle force is increased in mdx mice with reduced DNM2. Specific muscle force was measured in mdx$^{-/y}$ (white) and mdx$^{-/y}$ Dnm2$^{+/-}$ (black) mice, at 6 weeks, 3 months, and 1 year of age. Results are displayed as absolute force, relative to muscle mass (sPo/mg). Statistically significance is indicated as follows: *p<0.05, p<0.01, *p<0.001.
Figure 2:
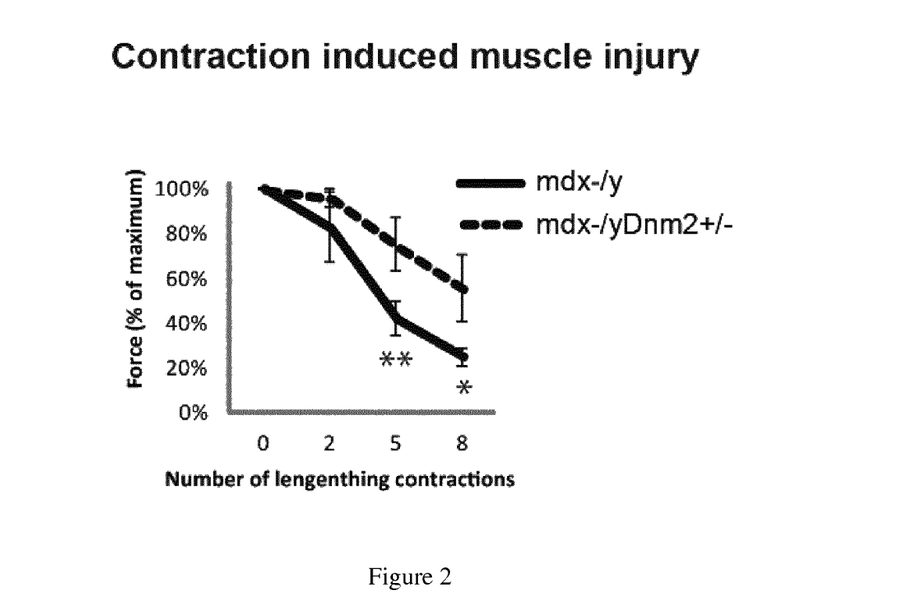
FIG. 2. Muscle force is improved following contraction-induced muscle injury, in mdx mice with reduced DNM2. Absolute muscle force was measured in mdx$^{-/y}$ (black, solid line) and mdx$^{-/y}$ Dnm2$^{+/-}$ (black, dashed line) mice at 1 year of age. Results are displayed as a percentage of initial force (%). Statistically significance is indicated as follows: *p<0.05, p<0.01, *p<0.001.

The Dynamin 2 inhibitor of the invention may also act by blocking and/or inhibiting the Dynamin 2 expression (including transcription, splicing, transcript maturation, or translation). The decrease or inhibition of Dynamin 2 expression can be evaluated by any means known to those skilled in the art including but not limited to assessing the level of Dynamin 2 protein using for instance Western Blot analysis (such as shown by FIG. 1) or ELISA, for example using an Anti-Dynamin 2 antibody, and/or assessing the level of mRNA for Dynamin 2 (such as shown by FIG. 2) using any available technique such as quantitative PCR for example.

The Dynamin 2 inhibitor is preferably selected from the group consisting of an antibody directed against Dynamin 2, a nucleic acid molecule interfering specifically with Dynamin 2 expression, and a small molecule inhibiting the Dynamin 2 enzymatic activity (i.e., inhibition of the GTPase activity), expression (such as by inhibiting promoter, splicing or translation), or function (such as inhibition of oligomerisation, activation, lipid binding, or partner binding).

According to a particular embodiment, the Dynamin 2 inhibitor is selected from the group consisting of an antibody directed against Dynamin 2 or a nucleic acid molecule (or nucleotide) interfering specifically with Dynamin 2 expression. In a preferred embodiment, the Dynamin 2 inhibitor is selected from the group consisting of a nucleic acid molecule interfering specifically with Dynamin 2 expression. According to the invention, the nucleic acid molecule interfering specifically with Dynamin 2 expression is usually a non-naturally occurring nucleic acid. In a particular embodiment, the Dynamin 2 inhibitor is a RNAi, an antisense nucleic acid or a ribozyme interfering specifically with Dynamin 2 expression.

In a particular embodiment, the Dynamin 2 inhibitor is a siRNA or shRNA.

In the present invention, the nucleic acid is capable of hybridizing specifically to a gene or transcripts coding for Dynamin 2. By "hybridizing specifically", is intended hybridized in stringent conditions. In particular, stringent conditions can be defined by salt concentration, the concentration of organic solvent, for example, formamide, temperature, and other conditions well known in the art. Typical stringent hybridisation conditions include temperatures above 30° C., preferably above 35° C., more preferably in excess of 42° C., and/or salinity of less than about 500 mM, preferably less than 200 mM. Nevertheless, it is understood that the nucleic acid according to the invention does not need to have 100% complementarity with the target sequence to hybridize specifically. In particular, a nucleic acid with a degree of complementarity at least equal to approximately 90% is capable of hybridizing specifically. Preferably, the degree of complementarity between the nucleic acid according to the invention and the target sequence is equal to at least 95%, 96%, 97%, 98%, 99% or 100%.

The term "complementary" or "complementarity" refers to the ability of polynucleotides to form base pairs with another polynucleotide molecule. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100 percent complementarity refers to the situation in which each nucleotide unit of one polynucleotide strand can bind to a nucleotide unit of a second polynucleotide strand. Less than perfect complementarity refers to the situation in which some, but not all, nucleotide units of two strands can bind with each other. For example, for two 20-mers, if only two base pairs on each strand can bind with each other, the polynucleotide strands exhibit 10 percent complementarity. In the same way, if 18 base pairs on each strand can be bond with each other, the polynucleotide strands exhibit 90 percent complementarity.

As used herein, the term "iRNA", "RNAi" or "interfering RNA" means any RNA which is capable of down-regulating the expression of the targeted protein. It encompasses small interfering RNA (siRNA), double-stranded RNA (dsRNA), single-stranded RNA (ssRNA), and short hairpin RNA (shRNA) molecules. RNA interference designates a phenomenon by which dsRNA specifically suppresses expression of a target gene at post-transcriptional level. In normal conditions, RNA interference is initiated by double-stranded RNA molecules (dsRNA) of several thousands of base pair length. In vivo, dsRNA introduced into a cell is cleaved into a mixture of short dsRNA molecules called siRNA. The enzyme that catalyzes the cleavage, Dicer, is an endo-RNase that contains RNase III domains (Bernstein, Caudy et al. 2001 Nature. 2001 Jan. 18; 409(6818):363-6). In mammalian cells, the siRNAs produced by Dicer are 21-23 bp in length, with a 19 or 20 nucleotides duplex sequence, two-nucleotide 3' overhangs and 5'-triphosphate extremities (Zamore, Tuschl et al. Cell. 2000 Mar. 31; 101(1):25-33; Elbashir, Lendeckel et al. Genes Dev. 2001 Jan. 15; 15(2): 188-200; Elbashir, Martinez et al. EMBO J. 2001 Dec. 3; 20(23):6877-88). According to a particular embodiment, iRNAs do not encompass microRNAs.

A number of patents and patent applications have described, in general terms, the use of siRNA molecules to inhibit gene expression, for example, WO 99/32619. RNA interference therapy by siRNA and shRNA is also detailed in the review by Z. Wang et al., Pharm Res (2011) 28:2983-2995.

siRNA or shRNA are usually designed against a region 19-50 nucleotides downstream the translation initiator codon, whereas 5'UTR (untranslated region) and 3'UTR are usually avoided. The chosen siRNA or shRNA target sequence should be subjected to a BLAST search against EST database to ensure that the only desired gene is targeted. Various products are commercially available to aid in the preparation and use of siRNA or shRNA.

In a preferred embodiment, the RNAi molecule is a siRNA of at least about 10-40 nucleotides in length, preferably about 15-30 base nucleotides.

siRNA or shRNA can comprise naturally occurring RNA, synthetic RNA, or recombinantly produced RNA, as well as altered RNA that differs from naturally-occurring RNA by the addition, deletion, substitution and/or alteration of one or more nucleotides. Such alterations can include addition of non-nucleotide material, such as to the end of the molecule or to one or more internal nucleotides of the siRNA, including modifications that make the siRNA resistant to nuclease digestion.

Some Dynamin 2 inhibitory nucleic acids are commercially available. One can cite for example, but not limited to: Abnova-Novus Biologicals, Dynamin 2 RNAi with references: H00001785-R05-H00001785-R08; Santa Cruz Biotechnology, Dynamin II siRNA (h) with reference: sc-35236, Dynamin II (h)-PR with reference: sc-35236-PR, Dynamin II shRNA Plasmid (h) with reference: sc-35236-SH, Dynamin II shRNA (h) Lentiviral Particles with reference: sc-35236-V).

In a particular embodiment, the nucleic acid molecule interfering specifically with Dynamin 2 is a nucleic acid interfering specifically with at least one part of the full length muscle human cDNA sequence of dynamin 2 (as shown in SEQ ID No 1, transcript variant 1 (NM_001005360.2)(exon 10a, 13ter) with 12b added). According to this embodiment, and more specifically, the RNAi molecule is a siRNA or shRNA of at least about 10-40 nucleotides in length, preferably about 15-30 base nucleotides iRNA. In a particular embodiment, siRNA or shRNA targets at least one exon of Dynamin2 mRNA, and more specifically at least one of exon 1, 4, 5, 12b, 13, 15, 17 and 21 of Dynamin2 mRNA.

In a particular embodiment, the nucleic acid molecule specifically interfering with Dynamin 2 comprises or consists of a sequence selected from the group consisting of iRNA sequence of SEQ ID No 2: 5'-AAGGACATGATCCTGCAGTTCAT-3'(or shRNA seq No C, below), iRNA sequence of SEQ ID No 3: 5'-AAGAGGCTACATTGGCGTGGTGA-3', iRNA sequence of SEQ ID No 4: 5'-AGGTGGACACTCTGGAGCTCTCC-3', iRNA sequence of SEQ ID No 5: 5'-AAGAAGTACATGCTGCCTCTGGA-3', iRNA sequence of SEQ ID No 6: 5'-AACGTCTACAAGGACCTGCGGCA-3', iRNA sequence of SEQ ID No 7: 5'-AGGAGAACACCTTCTCCATGGAC-3', iRNA sequence of SEQ ID No 8: 5'-AACTGTTACTATACTGAGCAG-3', iRNA sequence of SEQ ID No 9: 5'-TGCCAACTGTTACTATACT-3', iRNA sequence of SEQ ID No 10: 5'-GAAGAGCTGATCCCGCTGG-3', iRNA sequence of SEQ ID No 11: 5'-GCACGCAGCTGAACAAGAA-3', iRNA sequence of SEQ ID No 12: 5'-GGACTTACGACGGGAGATC-3', iRNA sequence of SEQ ID No 13: 5'-GGATATTGAGGGCAAGAAG-3', iRNA sequence of SEQ ID No 14: 5'-GGACCAGGCAGAAAACGAG-3', iRNA sequence of shRNA 15: 5'-GCGAATCGTCACCACTTAC-3'.

| shRNA against DNM2 | Target sequence | Dnm2 Exon target | SEQ ID No: |
|---|---|---|---|
| A | AACCGCGGGATGGAAGAGCT | 1 | 16 |
| B | AACTTGACCCTCATCGACCTC | 4 | 17 |
| C | AAGGACATGATCCTGCAGTTCAT | 4 | 2 |
| D | TCGGTGTCATCACCAAGCT | 5 | 18 |
| E | TGCCAACTGTTTCTATACT | 12b | 19 |
| F | AACTGTTTCTATACTGAGGAG | 12b | 20 |
| G | TTTCTATACTGAGGAGCTGGT | 12b | 21 |
| H | GCACGCAGCTGAACAAGAA | 13 | 22 |
| I | AAGAAGTACATGCTGCCTCTGGA | 15 | 23 |

-continued

| shRNA against DNM2 | Target sequence | Dnm2 Exon target | SEQ ID No: |
|---|---|---|---|
| J | AACACCTTCTCCATGGACCC | 17 | 24 |
| K | CCATTATCCGCCAGCCGAGC | 21 | 25 |

Antisense nucleic acid can also be used to down-regulate the expression of Dynamin 2. The antisense nucleic acid can be complementary to all or part of a sense nucleic acid encoding Dynamin 2, e.g., complementary to the coding strand of a double-stranded cDNA molecule or complementary to an mRNA sequence, and it is thought to interfere with the translation of the target mRNA. The antisense nucleic acids used in the invention interfere specifically with Dynamin 2 expression.

According to an embodiment, the antisense nucleic acid is a RNA molecule complementary to a target mRNA encoding Dynamin 2.

According to another embodiment, the antisense nucleotide denotes a single stranded nucleic acid sequence, either DNA or RNA, which is complementary to a part of a pre-mRNA encoding Dynamin 2. In particular, the antisense nucleotide of the present invention is designed to block a splice acceptor (SA) site and/or an exon splicing enhancer (ESE) and/or a branch point in the Dynamin2 pre-mRNA and/or any sequence which could modulate pre-mRNA splicing, i.e. it is designed to be complementary to a part of the Dynamin 2 pre-mRNA comprising an SA, an ESE, a branch point sequence or any sequence which could modulate pre-mRNA splicing. More specifically, the antisense nucleotide is used for inducing exon-skipping within a Dynamin 2 pre-mRNA, thereby leading to a frameshift which produces a truncated cDNA containing a premature stop codon in the resulting mRNA. This strategy thus allows the reduction of the level of DNM2 protein. In a particular embodiment, the antisense nucleotide is used for inducing exon-skipping within a Dynamin 2 pre-mRNA. For example, the implemented antisense nucleotide is designed to specifically induce exon 2 or exon 8 skipping. In a particular embodiment, the antisense nucleotide of the present invention is able to induce the inclusion of a premature stop codon in the human DNM2 mRNA. Skipping of exon 2 or exon 8 was shown to lead to an absence of the Dynamin 2 protein (as mentioned in "Reducing dynamin 2 expression rescues X-linked centronuclear myopathy". Cowling B S, Chevremont T, Prokic I, Kretz C, Ferry A, Coirault C, Koutsopoulos O, Laugel V, Romero N B, Laporte J., J Clin Invest. 2014 Mar. 3; 124(3):1350-63. doi: 10. 1172/JCI71206. Epub 2014 Feb. 24; and Tinelli E, Pereira J A, Suter U. Hum Mol Genet. 2013 Nov. 1; 22(21):4417-29. doi: 10.1093/hmg/ddt292. Epub 2013 Jun. 27).

In a particular embodiment, the antisense nucleotide is designed to specifically induce DNM2 exon 2 or exon 8 skipping, and comprises or consists of one of the following sequences:
U7-Ex2 (target skipping of DNM2 exon 2 with an antisense U7 snRNA), comprising the following sequence:

SEQ ID No 26:
GTCACCCGGAGGCCTCTCATTCTGCAGCTC

U7-Ex8 (target skipping of DNM2 exon 8 with an antisense U7 snRNA), comprising the following sequence:

SEQ ID No 27:
ACACACTAGAGTTGTCTGGTGGAGCCCGCATCA.

An antisense nucleic acid can be, for example, about 5, 10, 15, 20, 25, 30, 35, 40, 45 or 50 nucleotides in length. Particularly, antisense RNA molecules are usually 15-50 nucleotides in length. An antisense nucleic acid for use in the invention can be constructed using chemical synthesis and enzymatic ligation reactions using procedures known in the art. Particularly, antisense RNA can be chemically synthesized, produced by in vitro transcription from linear (e.g. PCR products) or circular templates (e.g., viral or non-viral vectors), or produced by in vivo transcription from viral or non-viral vectors. Antisense nucleic acid may be modified to have enhanced stability, nuclease resistance, target specificity and improved pharmacological properties. For example, antisense nucleic acid may include modified nucleotides or/and backbone designed to increase the physical stability of the duplex formed between the antisense and sense nucleic acids.

In the context of the invention "Ribozymes" are catalytic RNA molecules with ribonuclease activity which are capable of cleaving a single-stranded nucleic acid, such as an mRNA, to which they have a complementary region. Thus, ribozymes can be used to catalytically cleave mRNA transcripts to thereby inhibit translation of the protein encoded by the mRNA. Ribozyme molecules specific for functional Dynamin 2 can be designed, produced, and administered by methods commonly known to the art (see e.g., Fanning and Symonds (2006) *RNA Towards Medicine (Handbook of Experimental Pharmacology)*, ed. Springer p. 289-303).

Genome editing can also be used as a tool according to the invention. Genome editing is a type of genetic engineering in which DNA is inserted, replaced, or removed from a genome using artificially engineered nucleases, or "molecular scissors". The nucleases create specific double-stranded break (DSBs) at desired locations in the genome, and harness the cell's endogenous mechanisms to repair the induced break by natural processes of homologous recombination (HR) and non-homologous end-joining (NHEJ). There are currently four families of engineered nucleases being used: Zinc finger nucleases (ZFNs), Transcription Activator-Like Effector Nucleases (TALENs), the CRISPR/Cas system (more specifically Cas9 system, as described by P. Mali et al., in Nature Methods, vol. 10 No. 10, October 2013), or engineered meganuclease re-engineered homing endonucleases. Said nucleases can be delivered to the cells either as DNAs or mRNAs, such DNAs or mRNAs are engineered to target the DNM2 gene, according to the invention. According to an embodiment, Dynamin 2 inhibitor is a DNA or mRNA engineered to target the DNM2 gene and to deliver nucleases using genome editing therapy or is a nuclease engineered to target the DNM2 using genome editing therapy.

The nucleotides as defined above used according to the invention can be administered in the form of DNA precursors or molecules coding for them.

For use in vivo, the nucleotides of the invention may be stabilized, via chemical modifications, such as phosphate backbone modifications (e.g., phosphorothioate bonds). The nucleotides of the invention may be administered in free (naked) form or by the use of delivery systems that enhance stability and/or targeting, e.g., liposomes, or incorporated into other vehicles, such as hydrogels, cyclodextrins, biodegradable nanocapsules, bioadhesive microspheres, or proteinaceous vectors, or in combination with a cationic peptide. They can also be coupled to a biomimetic cell penetrating peptide. They may also be administered in the form of their precursors or encoding DNAs. Chemically stabilized versions of the nucleotides also include "Morpholinos" (phosphorodiamidate morpholino oligomers—PMO), 2'-O-Methyl oligomers, AcHN-(RXRRBR)2XB peptide-tagged PMO (R, arginine, X, 6-aminohexanoic acid and B,®-alanine) (PPMO), tricyclo-DNAs, or small nuclear (sn) RNAs. The latter forms of nucleotides that may be used to this effect are small nuclear RNA molecules including U1, U2, U4, U4atac, U5, U7, U11, and U12 (or other UsnRNPs), preferably U7snRNA (as identified above for SEQ ID No 26 and 27, in particular in combination with a viral transfer method based on, but not limited to, lentivirus, retrovirus, adenovirus or adeno-associated virus. All these techniques are well known in the art.

The nucleic acid molecule interfering specifically with Dynamin 2 expression of the invention may be delivered in vivo alone or in association with a vector. In its broadest sense, a "vector" is any vehicle capable of facilitating the transfer of the nucleotide to the cells and preferably cells expressing DNM2. Preferably, the vector transports the nucleotide to cells with reduced degradation relative to the extent of degradation that would result in the absence of the vector. In general, the vectors useful in the invention include, but are not limited to, plasmids, phagemids, viruses, and other vehicles derived from viral or bacterial sources that have been manipulated by the insertion or incorporation of the nucleotides of the invention. Viral vectors are a preferred type of vector and include, but are not limited to nucleic acid sequences from the following viruses: lentivirus such as HIV-1, retrovirus, such as moloney murine leukemia virus, adenovirus, adeno-associated virus; SV40-type viruses; Herpes viruses such as HSV-1 and vaccinia virus. One can readily use other vectors not named herein but known in the art. Among the vectors that have been validated for clinical applications and that can be used to deliver the nucleotides, lentivirus, retrovirus and Adeno-Associated Virus (AAV) show a greater potential for exon skipping strategy.

As used herein, the term "antibody" is intended to refer broadly to any immunologic binding agent such as IgG, IgM, IgA, IgD and IgE, and humanized or chimeric antibody. In certain embodiments, IgG and/or IgM are preferred because they are the most common antibodies in the physiological situation and they are most easily manufactured. The term "antibody" is used to refer to any antibody-like molecule that has an antigen binding region, and includes antibody fragments such as Fab', Fab, F(ab') 2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow, E. and Lane, D. (1988) *Antibodies: A Laboratory Manual*, ed., Cold Spring Harbor Laboratory).

A "humanized" antibody is an antibody in which the constant and variable framework region of one or more human immunoglobulins is fused with the binding region, e.g. the CDR, of an animal immunoglobulin. "Humanized" antibodies contemplated in the present invention are chimeric antibodies from mouse, rat, or other species, bearing human constant and/or variable region domains, bispecific antibodies, recombinant and engineered antibodies and fragments thereof. Such humanized antibodies are designed to maintain the binding specificity of the non-human antibody from which the binding regions are derived, but to avoid an immune reaction against the non-human antibody.

A "chimeric" antibody is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

Antibodies directed against Dynamin 2 are commercially available, such as antibodies sold or made by Novus Biologicals: catalogue numbers: Dynamin 2 Antibody NB300-617, Dynamin 2 Antibody NBP2-16244, Dynamin 2 Antibody (6C9) H00001785-M01, by Santa Cruz Biotechnology: catalogue number: sc-81150, sc-6400, sc-166525, sc-166669, sc-166526, by BD-Biosciences: anti-DNM2 (mouse ab, 610264), or by IGBMC-Illkirch: anti-DNM2: R2679, R2680, R2865, R2866, R2640, or R2641.

In another particular embodiment, the Dynamin 2 inhibitor is a small molecule inhibiting the Dynamin 2 enzymatic activity or function.

As used herein, the term "small molecule inhibiting Dynamin 2 activity, expression or function" refers to small molecule that can be an organic or inorganic compound, usually less than 1000 daltons, with the ability to inhibit or reduce the activity, expression or function of Dynamin 2. This small molecule can be derived from any known organism (including, but not limited to, animals, plants, bacteria, fungi and viruses) or from a library of synthetic molecules. Small molecules inhibiting Dynamin 2 activity, expression or function can be identified with the method described in this document.

Dynamin inhibitors are described in Harper C B et al., Trends Cell Biol. 2013 February; 23(2):90-101. Review. In a particular embodiment, such molecule is selected from the group consisting of:

Dynasore (a non-competitive, cell-permeable semicarbazone compound inhibitor of Dynamin 1 and Dynamin 2.—No CAS 304448-55-3), its chemical name is 3-Hydroxynaphthalene-2-carboxylic acid (3,4-dihydroxybenzylidene)hydrazide, Hydroxy-Dynasore (a highly potent inhibitor of dynamin 2 ($IC_{50}$=2.6 µM)) (Hydroxy-Dynasore is a cell-permeable hydroxylated analog of Dynamin Inhibitor, Dynasore—No CAS 1256493-34-1), its chemical name is 3-Hydroxy-N'-[(2,4,5-trihydroxyphenyl)methylidene] naphthalene-2-carbohydrazide, Tetradecyltrimethylammonium bromide (No CAS 1119-97-7), sold under the name MiTMAB™ (ab120466) by Abcam (a Cell permeable dynamin 1 and dynamin 2 inhibitor (IC50=8.4 µM for inhibition of dynamin II). It targets the pleckstrin homology (PH) (lipid binding) domain. It inhibits receptor-mediated and synaptic vesicle endocytosis (IC50 values 2.2 µM), Phthaladyn-23 (a cell-permeable phthalimide compound that is reported to inhibit Dynamin 2 GTPase activity ($IC_{50}$=63 µM)), the chemical name of Phthaladyn-23 is 4-Chloro-2-((2-(3-nitrophenyl)-1,3-dioxo-2,3-dihydro-1H-isoindole-5-carbonyl)-amino)-benzoic acid, Dynole 34-2, it is a Dynamin inhibitor V (scbt.com) and acts on GTPase activity, non-competitive for GTP, chemical name of Dynole 34-2 is 2-Cyano-N-octyl-3-[1-(3-dimethylaminopropyl)-1H-indol-3-yl]acrylamide, M-divi 1 (mitochondrial division inhibitor, IC50=10 µM) (scbt.com), the chemical name of M-divi-1 is 3-(2,4-Dichloro-5-methoxyphenyl)-2-sulfanylquinazolin-4(3H)-one, Iminodyn-22/17 (scbt.com) (Iminodyn 22: $IC_{50}$=390 nM acting on a GTPase allosteric site and displays uncompetitive antagonism with respect to GTP), the chemical name of Iminodyn 22 is N,N'-(Propane-1,3-diyl)bis(7,8-dihydroxy-2-imino-2H-chromene-3-carboxamide), the chemical name of Iminodyn 17 is N,N'-(Ethane-1,2-diyl)bis(7,8-dihydroxy-2-imino-2H-chromene-3-carboxamide), OcTMAB, i.e., OctadecylTriMethylAmmonium Bromide, (abcam.com), it targets the PH domain, Dynamin inhibitory peptide (Tocris Biosciences 1774): with amino acid sequence: SEQ ID No 28: QVPSRPNRAP, Dyngo-4a (IC50 –2.5 µM), it acts on a GTPase allosteric site, chemical name of Dyngo-4a is 3-Hydroxy-N'-[(2,4,5-trihydroxyphenyl)methylidene]naphthalene-2-carbohydrazide, RTIL-13 (IC50 –2.3 µM), it is a norcantharidin scaffold targeting the PH domain, chemical name of RTIL-13 is 4-(N,N-Dimethyl-N-octadecyl-N-ethyl)-4-aza-10-oxatricyclo-[5.2.1]decane-3,5-dione bromide.

Uses of Dynamin 2 Inhibitors

The invention relates to a method for treating DMD by administering a therapeutically effective amount of a Dynamin 2 inhibitor as defined above to patients in need thereof, and to the uses of such Dynamin 2 inhibitor in the treatment of DMD. It also relates to the use of a Dynamin 2 inhibitor for the manufacture of a pharmaceutical composition for the treatment of DMD. It relates to a Dynamin 2 inhibitor for use in the treatment of DMD.

Moreover, the present invention relates to a pharmaceutical composition comprising a Dynamin 2 inhibitor, and optionally a pharmaceutically acceptable carrier, in particular for use in the treatment of DMD.

In a particular embodiment of the invention, the disease to be treated is Duchenne's Muscular Dystrophy (DMD), more specifically by increasing muscle force of DMD patients and/or by improving the resistance of muscles to contraction induced injury.

As used herein, the term "therapeutically effective amount" is intended an amount of therapeutic agent, administered to a patient that is sufficient to constitute a treatment of a DMD. In a particular embodiment, the therapeutically effective amount to be administered is an amount sufficient to reduce the Dynamin 2 expression, activity or function in a level equal or less than the normal level. The normal level is the Dynamin 2 expression, activity or function of subjects that do not present DMD. The amount of Dynamin 2 inhibitor to be administered can be determined by standard procedure well known by those of ordinary skill in the art. Physiological data of the patient (e.g. age, size, and weight), the routes of administration and the disease to be treated have to be taken into account to determine the appropriate dosage, optionally compared with subjects that do not present DMD. One skilled in the art will recognize that the amount of Dynamin 2 inhibitor or of a vector containing or expressing the nucleic acid interfering specifically with Dynamin 2 expression to be administered will be an amount that is sufficient to induce amelioration of unwanted DMD symptoms or to induce alleviation of one or more symptoms or characteristics of DMD. An alleviation of one or more symptoms or characteristics may be assessed by any of the following assays on a myogenic cell or muscle cell from a patient: reduced calcium uptake by muscle cells, decreased collagen synthesis, altered morphology, altered lipid biosynthesis, decreased oxidative stress, and/or improved muscle fiber function, integrity, and/or survival. These parameters are usually assessed using immunofluorescence and/or histochemical analyses of cross sections of muscle biopsies. An alleviation of one or more symptoms or characteristics may also be assessed by any of the following assays on the patient self: prolongation of time to loss of walking, improvement of muscle strength, improvement of the ability to lift weight, improvement of the time taken to rise from the floor, improvement in the nine-meter walking time or 6 minute walk, improvement in the time taken for four-stairs climbing, improvement of the leg function grade, improvement of the pulmonary function, improvement of cardiac function, improvement of the quality of life. Each of these assays is known to the skilled person. For each of these assays, as soon as a detectable improvement or prolongation of a parameter measured in an assay has been found, it will preferably mean that one or more symptoms of Duchenne Muscular Dystrophy has been alleviated in an individual using the method of the invention. Detectable improvement or prolongation is preferably a statistically significant improvement or prolongation as described in Hodgetts et al (Hodgetts S., et al, (2006), Neuromuscular Disorders, 16: 591-602.2006). Alternatively, the alleviation of one or more symptom(s) of Duchenne Muscular Dystrophy may be assessed by measuring an improvement of a muscle fiber function, integrity and/or survival as later defined herein. The improvement of muscle fiber function, integrity and/or survival may be assessed using at least one of the following assays: a detectable decrease of creatine kinase in blood, a detectable decrease of necrosis of muscle fibers in a biopsy cross-section of a muscle suspected to be dystrophic, and/or a detectable increase of the homogeneity of the diameter of muscle fibers in a biopsy cross-section of a muscle suspected to be dystrophic. Each of these assays is known to the skilled person. The amount of Dynamin 2 inhibitor or of a vector containing or expressing the nucleic acid interfering specifically with Dynamin 2 expression may vary inter alia depending on such factors as the type of selected dynamin 2 inhibitors, the gender, age, weight, overall physical condition of the patient, etc. and may be determined on a case by case basis. The amount may also vary according to other components of a treatment protocol (e.g. administration of other medicaments, etc.). Generally, when the Dynamin 2 inhibitor is a nucleic acid, a suitable dose is in the range of from about 1 mg/kg to about 100 mg/kg, and more usually from about 2 mg/kg/day to about 10 mg/kg. If a viral-based delivery of the nucleic acid is chosen, suitable doses will depend on different factors such as the virus that is employed, the route of delivery (intramuscular, intravenous, intra-arterial or other), but may typically range from $10^{-9}$ to $10^{-15}$ viral particles/kg. If the inhibitor is a small molecule inhibiting the Dynamin 2 activity, expression or function, each unit dosage may contain, for example, from 2 to 300 mg/kg of body weight, particularly from 5 to 100 mg/kg of body weight. If the inhibitor is an antibody, each unit dosage may contain, for example, from 0.1 to 20 mg/kg of body weight, particularly from 4 to 10 mg/kg of body weight. Those of skill in the art will recognize that such parameters are normally worked out during clinical trials. Further, those of skill in the art will recognize that, while disease symptoms may be completely alleviated by the treatments described herein, this need not be the case. Even a partial or intermittent relief of symptoms may be of great benefit to the recipient. In addition, treatment of the patient may be a single event, or the patient is administered with the Dynamin 2 inhibitor on multiple occasions, that may be, depending on the results obtained, several days apart, several weeks apart, or several months, or even several years apart. A treatment in a method according to the invention may have a duration of at least one week, at least one month, at least several months, at least one year, at least 2, 3, 4, 5, 6 years or more. The frequency of administration may be ranged between at least once in a two weeks, or three weeks or four weeks or five weeks or a longer time period.

Each Dynamin 2 inhibitor as defined herein for use according to the invention may be suitable for direct administration to a cell, tissue and/or an organ in vivo of individuals affected by or at risk of developing DMD and may be administered directly in vivo, ex vivo or in vitro. An oligonucleotide as used herein may be directly or indirectly administrated to a cell, tissue and/or an organ in vivo of an individual affected by or at risk of developing DMD, and may be administered directly or indirectly in vivo, ex vivo or in vitro. As Duchenne muscular dystrophy has a pronounced phenotype in muscle cells, it is preferred that said cells are muscle cells, it is further preferred that said tissue is a muscular tissue and/or it is further preferred that said organ comprises or consists of a muscular tissue. A preferred organ is the heart. Preferably said cells are cells of an individual suffering from DMD.

A Dynamin 2 inhibitor as defined herein (which can be a molecule or oligonucleotide or equivalent thereof) can be delivered as is to a cell. When administering said inhibitor to an individual, it is preferred that it is dissolved in a solution that is compatible with the delivery method. For intravenous, subcutaneous, intramuscular, intrathecal and/or intraventricular administration, it is preferred that the solution is a physiological salt solution. Particularly preferred for a method of the invention is the use of an excipient that will further enhance delivery of said inhibitor as defined herein, to a cell and into a cell, preferably a muscle cell.

The pharmaceutical composition of the invention is formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Preferably, Dynamin 2 inhibitor as defined herein is dissolved in a solution that is compatible with the delivery method. For intravenous, subcutaneous, intramuscular, intrathecal and/or intraventricular administration, it is preferred that the solution is a physiological salt solution.

More generally, possible pharmaceutical compositions include those suitable for oral, rectal, mucosal, topical (including transdermal, buccal and sublingual), or parenteral (including subcutaneous, intramuscular, intravenous, intraarterial and intradermal) administration. For these formulations, conventional excipient can be used according to techniques well known by those skilled in the art.

More particularly, in order to provide a localized therapeutic effect, specific muscular administration routes are preferred. In particular, intramuscular administration is preferred.

Pharmaceutical compositions according to the invention may be formulated to release the active drug substantially immediately upon administration or at any predetermined time or time period after administration.

Within the context of the invention, the term treatment denotes curative, symptomatic, and preventive treatment. As used herein, the term "treatment" of a disease refers to any act intended to extend life span of subjects (or patients) such as therapy and retardation of the disease progression. The treatment can be designed to eradicate the disease, to stop the progression of the disease, and/or to promote the regression of the disease. The term "treatment" of a disease also refers to any act intended to decrease the symptoms associated with the disease, such as hypotonia and muscle weakness. Prolongation of time to loss of walking, improvement of muscle strength, improvement of the ability to lift weight, improvement of the time taken to rise from the floor, improvement in the 6 minute walk or nine-meter walking time, improvement in the time taken for four-stairs climbing, improvement of the leg function grade, improvement of the pulmonary function, improvement of cardiac function, or improvement of the quality of life of subjects (or patients) are also within the definition of the term "treatment". More specifically, the treatment according to the invention is intended to delay the appearance of the DMD phenotypes or symptoms, ameliorate the motor and/or muscular behavior and/or lifespan, in particular by improving muscle force and/or resistance to contraction-induced muscle injury.

The subject (or patient) to treat is any mammal, preferably a human being. Preferably the subject is a human patient, whatever its age or sex. New-borns, infants, children are included as well. More preferably, the patient or subject according to the invention is a Duchenne patient or is suspected to be a Duchenne patient (a patient susceptible to develop DMD because of his or her genetic background).

Screening of Dynamin 2 Inhibitors

The present invention also concerns a method for identifying or screening molecules useful in the treatment of DMD, based on the ability of such molecules to inhibit the expression, activity and/or function of Dynamin 2.

In particular, the invention is drawn to a method for screening comprising the steps of:

a) providing or obtaining a candidate compound, b) determining whether said candidate compound inhibits the activity, function and/or expression of Dynamin 2, and c) wherein the ability of said candidate compound to inhibit the expression, function or activity of said Dynamin 2 indicates that said candidate compound is indicative of its usefulness for the treatment of DMD.

The candidate compound to be tested in the frame of this method may be of any molecular nature, for example it may correspond to a chemical molecule (preferably a small molecule), an antibody, a peptide, a polypeptide, an aptamer, a siRNA, a shRNA, a snRNA, a sense or antisense oligonucleotide, a ribozyme, or a targeted endonuclease.

The ability of said candidate compound to inhibit the expression, activity or function of Dynamin 2 may be tested using any of the methods known to those skilled in the art, such as those identified above or described in the examples.

The method for screening or identifying a molecule suitable for the treatment of DMD can optionally further comprise the step of administering in vivo or in vitro selected molecule in DMD non-human animal model or a part thereof (tissue or cells, such as muscle tissue or cells) and analyzing the effect on the myopathy onset or progression.

As DMD non-human animal models, one can cite the dystrophin-deficient mdx mice. The dystrophin-deficient mdx mice is a classic model used for medical research into Duchenne's muscular dystrophy, which was first discovered 30 years ago (Bulfield, G., W. G. Siller, P. A. Wight and K. J. Moore (1984). "X chromosome-linked muscular dystrophy (mdx) in the mouse." *Proc Natl Acad Sci USA* 81(4): 1189-1192.). Mdx mice have a spontaneous mutation resulting in a premature stop codon in exon 23 of the dystrophin gene, and total loss of protein expression. The mdx mouse model has been used extensively used for research into the pathophysiology of DMD, and in testing potential therapies in preclinical approaches (Manning, J. and D. O'Malley (2015). "What has the mdx mouse model of duchenne muscular dystrophy contributed to our understanding of this disease?" *J Muscle Res Cell Motil.*). This model mice was used in the following examples.

The following examples are given for purposes of illustration and not by way of limitation.

EXAMPLES

Example 1

Materials:
Animal Experiments.

Animals were housed in a temperature-controlled room (19-22° C.) with a 12:12-hour light/dark cycle. When required mice were humanely sacrificed by $CO_2$ inhalation followed by cervical dislocation, according to national and European legislations on animal experimentation, and the tibialis anterior muscles were dissected and frozen in nitrogen-cooled isopentane and liquid nitrogen. Animal experimentation was approved by the institutional ethical committee Com'Eth IGBMC-ICS, and the French Ministry (approval number No 01594.01).

Mice Breedings:

Mdx mice, a spontaneously occurring mouse model for DMD which does not express dystrophin and present a mild dystrophic phenotype, were obtained by breeding males Homozygous for $Dmd^{mdx}$ and females Homozygous for $Dmd^{mdx}$ from Charles River Laboratories. Mdx mice were bred with $Dnm2^{+/-}$ mice to genetically downregulate DNM2. $Dnm2^{+/-}$ mice were generated and characterized by the host laboratory, as described previously (Cowling, B. S., T. Chevremont, I. Prokic, C. Kretz, A. Ferry, C. Coirault, O. Koutsopoulos, V. Laugel, N. B. Romero and J. Laporte (2014). "Reducing dynamin 2 expression rescues X-linked centronuclear myopathy." *J Clin Invest* 124(3): 1350-1363).

In Situ Muscle Force:

Tibialis anterior maximal muscle force was measured in situ in $mdx^{-/y}$ and $mdx^{-/y}$ $Dnm2^{+/-}$ mice at 6 weeks, 3 months, and at one year of age, using the Whole Mouse Test System (Aurora 1300A). The sciatic nerve was stimulated, and the total force produced by contraction of the tibialis anterior muscle was measured, as described previously (Cowling et al. 2014). Specific muscle force was calculated as a ratio of maximal muscle force relative to muscle mass.

Contraction-induced muscle injury: Susceptibility to contraction-induced muscle injury was measured using the Whole Mouse Test System (Aurora 1300A) at one year of age, as described previously (Hourde et al. 2013). The decrease in absolute muscle force resulting from several damage-inducing lengthening contractions was measured. Initially the sciatic nerve was stimulated (700 milliseconds, frequency 150 Hz), and the isometric muscle force produced was measured, followed by 8 lengthening (+10% length) contractions, in which isometric muscle force was measured (at the initial length) after each contraction. Force is represented at a percentage of initial force produced. Data is represented as the percentage of initial force, after 2, 5, and 8 lengthening contractions. After contractile measurements, the animals were euthanized with an overdose of pentobarbital, and tibialis anterior muscles were weighed.

Results:

Physiological improvement in muscle function was tested by measurement of specific muscle force of the tibialis anterior muscle, in situ. When the sciatic nerve was stimulated, absolute muscle force was measured. Specific muscle force was then calculated as a ratio of total muscle force compared to muscle fiber mass. In $mdx^{-/y}$ mice with reduced DNM2 expression ($mdx^{-/y}$ $Dnm2^{+/-}$), specific muscle force was increased at 6 weeks and 3 months of age, compared to control $mdx^{-/y}$ mice (FIG. 1).

In order to confirm the physiological significance of this improvement in muscle force. Similar to patients with Duchenne muscular dystrophy (DMD), skeletal muscles from $mdx^{-/y}$ mice lack dystrophin, and are known to be more susceptible to contraction-induced injury than healthy controls. Mice were therefore submitted to lengthening muscle contractions which induces damage to muscle fibers, to analyze the susceptibility of mdx dystrophic muscles to damage, when DNM2 expression is reduced.

8 lengthening contractions, inducing muscle fiber damage, were performed, and maximum muscle force was measured after each contraction. Importantly $mdx^{-/y}$ $Dnm2^{+/-}$ mice exhibited a 2-fold increase in resistance to contraction-induced injury, compared to $mdx^{-/y}$ mice (FIG. 2). Therefore reducing DNM2 improves the resistance of mdx muscles to contraction induced injury.

Conclusions:

Reducing DNM2 expression has thus therapeutic potential in Duchenne's Muscular Dystrophy. It was indeed shown a significant improvement in specific muscle force at several ages by reducing DNM2 in mdx mice, which are the classic mouse model used for preclinical DMD research. Furthermore, a two-fold improvement is seen in resistance to contraction-induced muscle injury, confirming the physiological significance of this finding. Therefore, reducing DNM2 is a novel therapeutic target for Duchenne's muscular dystrophy.

Example 2

Materials and Methods:
Production and Purification of AAV:

AAV2/9 vectors were generated by a triple transfection of AAV-293 cell line with pAAV2 insert containing the insert under the control of the CMV promoter and flanked by serotype 2 inverted terminal repeats, pXR1 containing rep and cap genes of AAV serotype 9, and pHelper encoding the adenovirus helper functions. Cell lysates were subjected to 3 freeze/thaw cycles, then treated with 50 U/mL of Benzonase (Sigma) for 30 minutes at 37° C., and clarified by centrifugation. Viral vectors were purified by Iodixanol gradient ultracentrifugation followed by dialysis and concentration against Dulbecco's Phosphate Buffered Saline using centrifugal filters (Amicon Ultra-15 Centrifugal Filter Devices 30K, Millipore, Bedford). Physical particles were quantified by real-time PCR using a plasmid standard pAAV-eGFP, and titers are expressed as viral genomes per milliliter (vg/mL). rAAV titers used in these experiments were 5 to 7 $10^{11}$ vg/mL.

AAV Transduction of Mdx–/y Tibialis Anterior (T.A) Muscles of Mice:

3-week-old, male, mdx–/y mice were anesthetized by i.p. injection of 5 µl/g of ketamine (20 mg/mL; Virbac, Carros, France) and xylazine (0.4%, Rompun; Bayer, Wuppertal, Germany). An intramuscular injection of AAV2/9-shRNA targeting DNM2 (black) or a AAV2/9 scrambled control sequence (white) was performed into the tibialis anterior of mdx−/y mice at 3 weeks of age. Animals were housed in a temperature-controlled room (19° C. to 22° C.) with a 12:12-hour light/dark cycle.

Mice breedings were as described in example 1.

Results:

Muscle force following contraction-induced muscle injury, in mdx mice with reduced DNM2.

Figure 3:
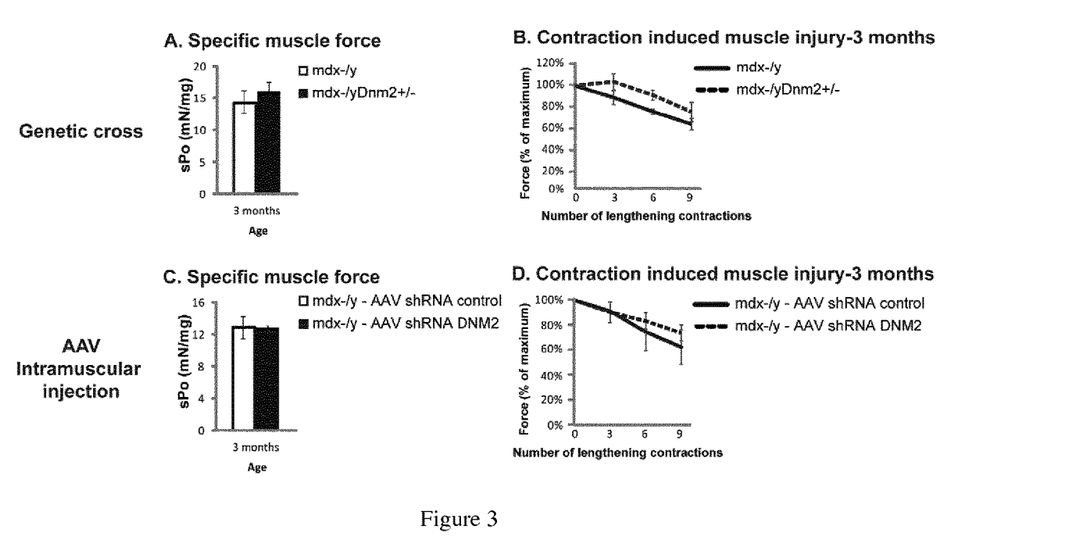

Mdx−/y and mdx−/yDnm2+/− mice were analyzed for muscle force. Specific muscle force (sPo) was initially measured in the tibialis anterior muscle from mdx−/y (white) and mdx−/yDnm2+/−(black) mice (see FIG. 3A). Following this the tibialis anterior muscle was subjected to 9 lengthening contractions. Results for mdx−/y (solid black line) and mdx−/yDnm2+/− (dashed black line) mice are displayed as a percentage of initial force (%), after 0, 3, 6 and 9 lengthening contractions (see FIG. 3B).

Mdx−/y mice at 3 weeks of age were injected with AAV2/9-shRNA targeting DNM2 (black) or an AAV2/9 scrambled control sequence (white) into the tibialis anterior muscles. Specific muscle force (sPo) was measured in the tibialis anterior muscle at 3 months of age (see FIG. 3C). The tibialis anterior muscle was then subjected to 9 lengthening contractions as in FIG. 3 B (see FIG. 3D), AAV shRNA control (solid black line) and AAV shRNA DNM2 (dashed black line).

All mice were 3 months old at age of analysis. n=7-10 mice/group. All graphs represent mean+s.e.m.

Both FIGS. 3B and 3D mdx−/y mice with reduced DNM2 (dashed black line) display a trend towards resistance to contraction-induced injury.

Conclusions:

Mdx mice were crossed with Dnm2+/− mice or subjected to intramuscular injection of AAV expressing shRNA targeting Dnm2 to reduce the level of DNM2. At 3 months of age, while there was no significant difference in specific muscle force between the groups, a trend for increased resistance to contraction-induced injury was observed for both techniques.

The invention claimed is:

1. A method for the treatment of Duchenne's muscular dystrophy, wherein the method comprises the step of administering into a subject in need of such treatment a therapeutically efficient amount of a Dynamin 2 inhibitor, wherein the Dynamin 2 (DNM2) inhibitor is an antisense nucleotide designed to specifically induce DNM2 exon 2 or exon 8 skipping, and comprises one of the following sequences:

U7-Ex2 (target skipping of DNM2 exon 2), comprising the following sequence: SEQ ID NO: 26: GTCACCCGGAGGCCTCTCATTCTGCAGCTC; or U7-Ex8 (target skipping of DNM2 exon 8), comprising the following sequence: SEQ ID NO: 27: ACACACTAGAGTTGTCTGGTGGAGCCCGCATCA.

2. The method according to claim 1, wherein the Dynamin 2 inhibitor comprises SEQ ID NO: 26.

3. The method according to claim 1, wherein the Dynamin 2 inhibitor comprises SEQ ID NO: 27.

4. A method for the treatment of Duchenne's muscular dystrophy comprising administering to a subject in need of such treatment a therapeutically efficient amount of a Dynamin 2 inhibitor, wherein the Dynamin 2 inhibitor is a nucleic acid molecule specifically interfering with Dynamin 2 and comprising SEQ ID NO: 2, 3, 4, 5, 6, 7, 8, 9, 10, 11, 12, 13, 14, 15, 16, 17, 18, 19, 20, 21, 22, 23, 24, or 25.

5. The method according to claim 4, wherein the Dynamin 2 inhibitor comprises SEQ ID NO: 2, 3, 4, or 5.

6. The method according to claim 5, wherein the Dynamin 2 inhibitor comprises SEQ ID NO: 6, 7, 8, or 9.

7. The method according to claim 4, wherein the Dynamin 2 inhibitor comprises SEQ ID NO: 10, 11, 12, or 13.

8. The method according to claim 4, wherein the Dynamin 2 inhibitor comprises SEQ ID NO: 14, 15, 16, or 17.

9. The method according to claim 4, wherein the Dynamin 2 inhibitor comprises SEQ ID NO: 18, 19, 20, or 21.

10. The method according to claim 4, wherein the Dynamin 2 inhibitor comprises SEQ ID NO: 22, 23, 24, or 25.

* * * * *

UNITED STATES PATENT AND TRADEMARK OFFICE
CERTIFICATE OF CORRECTION

| | | |
|---|---|---|
| PATENT NO. | : 10,822,400 B2 | Page 1 of 1 |
| APPLICATION NO. | : 15/568007 | |
| DATED | : November 3, 2020 | |
| INVENTOR(S) | : Jocelyn Laporte and Belinda Cowling | |

It is certified that error appears in the above-identified patent and that said Letters Patent is hereby corrected as shown below:

In the Claims

<u>Column 30,</u>
Line 20, Claim 6, "The method according to claim 5" should read --The method according to claim 4--.

Signed and Sealed this
Fifth Day of October, 2021

Drew Hirshfeld
*Performing the Functions and Duties of the
Under Secretary of Commerce for Intellectual Property and
Director of the United States Patent and Trademark Office*